(12) United States Patent
Kim (10) Patent No.: US 10,946,060 B2
(45) Date of Patent: Mar. 16, 2021

(54) PHARMACEUTICAL COMPOSITION CONTAINING ATPIF1 FOR TREATMENT OF DIABETES

(71) Applicant: KOREA UNIVERSITY RESEARCH AND BUSINESS FOUNDATION, Seoul (KR)

(72) Inventor: Hyeon Soo Kim, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 0 days.

(21) Appl. No.: 16/494,293

(22) PCT Filed: Mar. 13, 2018

(86) PCT No.: PCT/KR2018/002933
§ 371 (c)(1),
(2) Date: Sep. 14, 2019

(87) PCT Pub. No.: WO2018/169282
PCT Pub. Date: Sep. 20, 2018

(65) Prior Publication Data
US 2020/0129581 A1    Apr. 30, 2020

(30) Foreign Application Priority Data
Mar. 17, 2017   (KR) .................. 10-2017-0033742

(51) Int. Cl.
| A61K 38/17 | (2006.01) |
| A61K 38/00 | (2006.01) |
| A61P 3/04  | (2006.01) |
| A61P 3/10  | (2006.01) |
| A61K 38/28 | (2006.01) |

(52) U.S. Cl.
CPC ........ *A61K 38/005* (2013.01); *A61K 38/1709* (2013.01); *A61K 38/28* (2013.01); *A61P 3/04* (2018.01); *A61P 3/10* (2018.01)

(58) Field of Classification Search
CPC ............... A61K 38/1709; C07K 14/47; C07K 14/4703; C07K 14/4705
See application file for complete search history.

(56) References Cited

U.S. PATENT DOCUMENTS

| 2002/0091081 A1* | 7/2002 | Papathanassiu ....... C07K 16/28 514/13.3 |
| 2004/0072739 A1 | 4/2004 | Anderson et al. |
| 2015/0065556 A1 | 3/2015 | Birsoy et al. |

FOREIGN PATENT DOCUMENTS

| KR | 101058290 A | 8/2011 |
| KR | 1020110111267 A | 10/2011 |
| KR | 1020110134209 A | 12/2011 |
| KR | 101330868 A | 11/2013 |
| KR | 1020140106452 A | 9/2014 |
| WO | WO9632478 A | 10/1996 |
| WO | WO9734631 A | 9/1997 |
| WO | WO-9833909 A1 * | 8/1998 ......... C07K 14/4703 |

OTHER PUBLICATIONS

Cabezon, E., et al., "Homologous and Heterologous Inhibitory Effects of ATPase Inhibitor Proteins on F-ATPases", "The Journal of Biological Chemistry", 2002, pp. 41334-41341, vol. 277, No. 44.
Chen, H.C., et al., "Inhibition of Triglyceride Synthesis as a Treatment Strategy for Obesity Lessons From DGAT1-Deficient Mice", "Arterioscler Thromb Vasc Biol", 2005, pp. 482-486, vol. 25.
Cooke, D., et al., "The Obesity Pipeline: Current Strategies in the Development of Anti-Obesity Drugs", "Nature Reviews Drug Discovery", Nov. 2006, pp. 919-1200, vol. 5.
Cypess, A.M., et al., "Brown Fat as a Therapy for Obesity and Diabetes", "Curr Opin Endocrinol Diabetes Obes.", Apr. 2010, pp. 143-149, vol. 17, No. 2.
Formentini, L., et al., "Mitochondrial H+-ATP Synthase in Human Skeletal Muscle: Contribution to Dyslipidaemia and Insulin Resistance", "Diabetologia", Oct. 2017, pp. 2052-2065, vol. 60, No. 10.
Garcia-Bermudez, J., et al., "The ATPase Inhibitory Factor 1 (IF1): a Master Regulator of Energy Metabolism and of Cell Survival", "Biochimica et Biophysica Acta", 2016, pp. 1167-1182.
Genoux, A., et al., "Mitochondrial Inhibitory Factor 1 (IF1) is Present in Human Serum and is Positively Correlated with HDL-Cholesterol", "PLoS One", Sep. 2011, p. e23949; 1-8, vol. 6.
Genoux, A., et al., "Serum Levels of Mitochondrial Inhibitory Factor 1 are Independently Associated With Long-Term Prognosis in Coronary Artery Disease: the Genes Study", "BMC Medicine", 2016, pp. 1-10, vol. 14, No. 125.
Hardie, D., "AMPK: a Key Regulator of Energy Balance in the Single Cell and the Whole Organism", "International Journal of Obesity", 2008, pp. S7-S12, vol. 32.
Lightfoot, A.P., et al., "The Role of Myokines in Muscle Health and Disease", "Current Opinion Rheumatol.", 2016, pp. 661-666, vol. 28, No. 6.

(Continued)

*Primary Examiner* — Jeffrey E. Russel
(74) *Attorney, Agent, or Firm* — Hultquist, PLLC; Steven J. Hultquist (57) ABSTRACT

The present invention relates to a pharmaceutical composition containing ATPase inhibitor factor 1 (ATPIF1) as an active ingredient for the prevention or treatment of diabetes or diabetic complications, and to a pharmaceutical composition containing ATP1F1 as an active ingredient for prevention or treatment of obesity. The composition containing ATPIF1, according to the present invention, has a diabetes treatment effect by promoting sugar absorption in muscle cells and improving insulin sensitivity, and has an obesity prevention or treatment effect by effects of suppressing fat synthesis in fat cells and promoting the browning of fat cells.

4 Claims, 5 Drawing Sheets

Specification includes a Sequence Listing.

(56) References Cited

OTHER PUBLICATIONS

Van Raaij, M., et al., "The ATPase Inhibitor Protein From Bovine Heart Mitochondria: the Minimal Inhibitory Sequence", "Biochemistry", 1996, pp. 15618-15625, vol. 35.

Whitham, M., et al., "The Ever-Expanding Myokinome: Discovery Challenges and Therapeutic Implications", "Nature Reviews Drug Discovery", 2016, pp. 719-729, vol. 15.

Shanik, M., et al., Insulin Resistance and Hyperinsulinernia, Diabetes Care, Feb. 2008, pp. S262-S268, vol. 31, No. 32.

Ishibazawa, A., et al., Characteristics of Retinal Neovascularization in Proliferative Diabetic Retinopathy Imaged by Optical Coherence Tomography Angiography, Investigative Ophthalmology & Visual Science Nov. 2016, vol. 57, 6247-6255. doi:https://doi.org/10.1167/iovs.16-20210.

Nakamura, J., et al., "IF1, a natural inhibitor of mitochondrial ATP synthase, is not essential for the normal growth breeding of mice", Biosci. Rep., 2013, 33(5), art:e0067.doi:10.1042/BSR20130078.

\* cited by examiner

FIG. 1

A ATPIF1 (60 ng/ml)   0   15   30   60   180   360   (min)

IB: p-AMPK (Thr$^{172}$)

IB: AMPK

B ATPIF1   0   6   20   60   200   600   (ng/ml)

IB: p-AMPK (Thr$^{172}$)

IB: AMPK

FIG. 2

A ATPIF1 (60 ng/ml)   0   15   30   60   180   360   (min)

IB: p-Akt (Ser$^{473}$)

IB: Akt

B ATPIF1   0   6   20   60   200   600   (ng/ml)

IB: p-Akt (Ser$^{473}$)

IB: Akt

ATPIF1      −   +   +   −
LY2940002   −   −   +   +

```
SEQUENCE LISTING

<160> NUMBER OF SEQ ID NOS: 7

<210> SEQ ID NO 1
<211> LENGTH: 81
<212> TYPE: PRT
<213> ORGANISM: Artificial Sequence
<220> FEATURE:
<223> OTHER INFORMATION: ATPIF1(ATPase inhibitor factor 1)

<400> SEQUENCE: 1

Gly Ser Asp Gln Ser Glu Asn Val Asp Arg Gly Ala Gly Ser Ile Arg
1               5                   10                  15

Glu Ala Gly Gly Ala Phe Gly Lys Arg Glu Gln Ala Glu Glu Glu Arg
            20                  25                  30

Tyr Phe Arg Ala Gln Ser Arg Glu Gln Leu Ala Ala Leu Lys Lys His
        35                  40                  45

His Glu Glu Glu Ile Val His His Lys Lys Glu Ile Glu Arg Leu Gln
    50                  55                  60

Lys Glu Ile Glu Arg His Lys Gln Lys Ile Lys Met Leu Lys His Asp
65                  70                  75                  80

Asp

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttggagagag agcgtccaat                                                    20
```

```
<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ctcaaagaag gccacaaagc                                               20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
caggaggagc aatgatcttg a                                             21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
actacctcat gaagatcctc a                                             21

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ctgcctctct cggaaacaag                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gccacaaacc ctttgaaaaa                                               20
```

PHARMACEUTICAL COMPOSITION CONTAINING ATPIF1 FOR TREATMENT OF DIABETES

CROSS-REFERENCE TO RELATED APPLICATIONS

This application is a U.S. national phase under the provisions of 35 U.S.C. § 371 of International Patent Application No. PCT/KR18/02933 filed Mar. 13, 2018, which in turn claims priority of Korean Patent Application No. 10-2017-0033742 filed Mar. 17, 2017. The disclosure of such International Patent Application No. PCT/KR18/02933 is hereby incorporated herein by reference in its entirety, for all purposes.

REFERENCE TO SEQUENCE LISTING SUBMITTED VIA EFS-WEB

This application includes an electronically submitted sequence listing in .txt format. The .txt file contains a sequence listing entitled "488SeqListing_ST25.txt" created on Sep. 14, 2019 and is 2242 bytes in size. The sequence listing contained in this .txt file is part of the specification and is hereby incorporated by reference herein in its entirety.

TECHNICAL FIELD

The present invention relates to a pharmaceutical composition for preventing or treating diabetes or diabetic complications containing ATPase inhibitor factor 1 (ATPIF1) as an active ingredient and a pharmaceutical composition for preventing or treating obesity containing ATPIF1 as an active ingredient.

BACKGROUND ART

Muscle has been known to serve as a skeleton to support the structure of the human body and to be involved in motion (exercise) through contraction and relaxation thereof, but has more recently been known to also function as an endocrine organ. In the mid-1980s, adipose tissue was found as a novel endocrine organ, the substance secreted from the adipose tissue was called "adipokine", and currently known adipokines including leptin, adiponectin, resistin and so on. Adipokines have been discovered to have a variety of functions including not only functions associated with fat synthesis but also functions associated with immunity, metabolism, nerves and cancer. Recently, it was discovered that a certain substance is secreted when skeletal muscle contracts, and this was identified to be a myokine, which was once called an "exercise factor". Many types of myokines are considered as novel target substances for disease research (Whitham M, et al., Nat Rev Drug Discov. 15:719-29, 2016; Lightfoot AP, et al., Curr. Opin. Rheumatol., 28:661, 2016).

Meanwhile, metabolic syndrome, which is accompanied by various diseases such as diabetes, obesity, hypertension, hyperlipidemia and atherosclerosis, has been observed to be a main cause of death in modern society by the World Health Organization (WHO). A method for treating and managing metabolic syndrome has not been established to date and recent studies showed that lack of exercise is the most important pathophysiological cause of diabetes and obesity. Therefore, the fundamental understanding of muscle contraction involved in exercise and secreted substances is required for overall treatment. Therefore, research on myokines, which are substances secreted from muscles, is expected to be capable not only of solving current medical problems, but also of leading to considerable economic, industrial and technical ripple effects.

According to a 2015 report by the American Drug Development Association, new drugs related to metabolic syndrome for more than 200 targets are being developed, and, taking into consideration about the current globally competitive research trend, myokine is a potential target for drug development. Research on myokines is known to be performed by Amrad, Genvec, Novartis and the Northwestern University of the United States.

Unlike foreign countries, which focus on the development of targets based on mechanisms of action, Korea has a lack of basic research results and insufficient medical industry application results. Recently, research on myokine has been conducted in some laboratories, and some research achievements have been made, but there are no research attempts to develop new drugs.

Thus, the present inventors have made intense efforts to find myokine, which has a function of controlling glucose uptake and fat metabolism in adipocytes. As a result, the present inventors have found that ATPase inhibitor factor (ATPIF1), which is a protein known to inhibit mitochondrial ATP synthesis in muscle cells, is capable of controlling glucose in muscle cells and fat metabolism in adipocytes. Based on this finding, the present invention has been completed.

DISCLOSURE

Therefore, it is one object of the present invention to provide a composition for the prevention or treatment of diabetes or diabetic complications containing myokine functioning to regulate glucose uptake.

It is another object of the present invention to provide a composition for the prevention or treatment of obesity containing myokine functioning to regulate fat metabolism in adipocytes.

In accordance with one aspect of the present invention, the above and other objects can be accomplished by the provision of a pharmaceutical composition for the prevention or treatment of diabetes or diabetic complications containing ATPIF1 (ATPase inhibitor factor 1) as an active ingredient.

In accordance with another aspect of the present invention, there is a provided method of preventing or treating diabetes or diabetic complications including administering ATPIF1 (ATPase inhibitor factor 1).

In accordance with another aspect of the present invention, there is provided a use of ATPIF1 (ATPase inhibitor factor 1) for the prevention or treatment of diabetes or diabetic complications.

In accordance with another aspect of the present invention, there is provided a use of ATPIF1 (ATPase inhibitor factor 1) for manufacturing medicament for treating or preventing diabetes or diabetic complications.

In accordance with another aspect of the present invention, there is provided a pharmaceutical composition for preventing or treating obesity containing ATPIF1 (ATPase inhibitor factor 1) as an active ingredient.

In accordance with another aspect of the present invention, there is provided a method of preventing or treating obesity including administering ATPIF1 (ATPase inhibitor factor 1).

In accordance with another aspect of the present invention, there is provided a use of ATPIF1 (ATPase inhibitor factor 1) for the prevention or treatment of obesity.

In accordance with another aspect of the present invention, there is provided a use of ATPIF1 (ATPase inhibitor factor 1) for manufacturing medicament for treating or preventing obesity.

DESCRIPTION OF DRAWINGS

FIGS, 5A and 5B show Western blot results showing the increase in glucose uptake due to ATPIF1in muscle cell lines, with FIG. 5A showing glucose uptake of muscle cells increased by ATPIF1, and with FIG. 5B showing that treatment with LY294002 inhibiting PI3K, and with compound C inhibiting AMPK, eliminated increase in glucose uptake by ATPIF1, indicating that PI3K and AMPK are involved in the glucose uptake process.

BEST MODE

Unless defined otherwise, all technical and scientific terms used herein have the same meanings as appreciated by those skilled in the field to which the present invention pertains. In general, the nomenclature used herein is well-known in the art and is ordinarily used.

ATPIF1 is considered to bind to ATPase at the alpha-beta interface to form a one-to-one complex with ATPase, which prevents the release of ATP to inhibit ATP synthesis (van Raaij M J et al., Biochemistry. 35: 15618, 1996). ATPIF1 has two oligomeric dimers (active state) and tetramers, and forms dimers through reverse parallel coiled-coil interactions between the C-terminal regions of two monomers at a low pH. At a high pH, inhibitors form tetramers and higher oligomers through coiled-coil interactions including the N-terminal and inhibition regions, thereby suppressing inhibitory activity (Cabezon E et al., J. Biol. Chem. 277: 41334, 2002).

ATPIF1 (ATPase inhibitor factor 1) is a protein that functions to inhibit mitochondrial ATP synthesis. The present invention first identified that ATPIF1 has the functions of controlling glucose in muscle cells and fat metabolism in adipocytes. In the present invention, the phosphorylation level of AMPK (AMPK-activated protein kinase), the phosphorylation of Akt, which is an insulin signal downstream substance, the expression of Glut4 proteins and mRNAs, and glucose uptake using isotopes were compared through experiments in order to demonstrate the glycemic control mechanism of ATPIF1 in muscle cell line. In addition, experiments were conducted on UCP1 (uncoupling protein 1), which is a marker gene of phosphorylation and fat-browning of the acetyl-CoA carboxylase (ACC), in order to investigate the association of ATPIF1 with fat synthesis in adipocyte lines.

The experiments identified that ATPIF1 exhibits a glycemic control effect by increasing the activity of AMPK and Akt in muscle cells and also has applicability as a drug (preparation) capable of overcoming type 2 diabetes by exhibiting a function as an insulin sensitizer that can overcome insulin tolerance.

Thus, in one aspect, the present invention is directed to a pharmaceutical composition for the prevention or treatment of diabetes or diabetic complications containing ATPIF1 (ATPase inhibitor factor 1) as an active ingredient.

To date, major proteins involved in glycemic control include Akt, AS (Akt substrate) 160, PKCzeta and the like, and are known to mainly act on the transport of glucose transporter proteins. In addition, diseases associated with the mechanism of occurrence at the molecular levels for glucose, urine and the like is considered to be caused by abnormality of the post-receptor process, in particular, abnormality of signaling between proteins through phosphoinositide-3 kinase (PI-3 kinase), rather than defects in the insulin receptor. Therefore, it is important to discover new target proteins related to glycemic control and to identify the molecular mechanisms thereof, since the therapeutic effect of insulin on diabetes is limited.

In the present invention, the diabetes may be type diabetes or initial type 2 diabetes, and the diabetes complications may be diabetic nephropathy, diabetic retinopathy, hyperlipidemia, fatty liver, or the like.

In the present invention, the ATPIF1 (ATPase inhibitor factor 1, SEQ ID NO: 1) can promote insulin sensitivity. Thus, the present invention may further include insulin or an insulin analogue.

In another aspect, the present invention is directed to a method of preventing or treating diabetes or diabetic complications including administering ATPIF1 (ATPase inhibitor factor 1).

In another aspect, the present invention is directed to a use of ATPIF1 (ATPase inhibitor factor 1) for the treatment or prevention of diabetes or diabetic complications.

In another aspect, the present invention is directed to a use of ATPIF1 (ATPase inhibitor factor 1) for manufacturing medicament for treating or preventing diabetes or diabetic complications.

As herein used, the term "diabetes" means a metabolic disease involving insufficient insulin secretion, insulin malfunctions or the like. By co-administering the composition of the present invention to a subject, diabetes can be treated by controlling blood glucose.

As used herein, the term "prevention" refers to any action that prevents or delays diabetes by co-administration of the composition of the present invention, and, as used herein, the term "treatment" refers to any action that improves or positively alters the symptoms of diabetes by the co-administration of the composition of the present invention. The diabetes treatment is applicable to any mammal that may be afflicted with diabetes, including, but not limited to, humans and primates, as well as domestic animals such as cattle, pigs, sheep, horses, dogs and cats, but preferably humans.

As used herein, the term "administration" refers to an action of introducing the pharmaceutical composition according to the present invention into a subject by any appropriate method, and the route of administration of the composition may be any general route, so long as it enables the composition to be delivered to a target tissue. The pharmaceutical composition may be administered intraperitoneally, intravenously, intramuscularly, subcutaneously, intradermally, orally, topically, intranasally, intrapulmonarily or rectally, but is not limited thereto. Upon oral administration, peptides are digested, so that an oral composition may be coated with an active drug or may be formulated so as to protect the same from degradation in the stomach.

Preferably, the composition may be administered in the form of an injection. In addition, a sustainable preparation may be administered by any device capable of delivering the active substance to the target cell.

In addition, the pharmaceutical composition of the present invention is determined according to the type of drug, which is the active ingredient, as well as various related factors such as the disease to be treated, the route of administration, the age, gender and body weight of the patient, and the severity of the disease.

In the present invention, insulin includes any peptide and modified peptide having insulin-receptor-stimulating activity, for example, an insulin analogue or a fragment thereof, in which some amino acids in natural insulin, fast-acting insulin, basal insulin and natural insulin are varied by any one method of substitution, addition, deletion and modification, or a combination thereof. In addition, in the present invention, the insulin may be sustained insulin, to which a sustained technology is applied, in order to overcome the short half-life thereof. Preferably, the insulin is sustained insulin or a sustained insulin analogue which can be administered once a week. Some specific examples of the insulin according to the present invention include insulins or insulin analogues and sustained forms thereof described in Korean Patent No. 10-1058290, and Korean Patent Application Nos. 10-2014-0022909 and 10-2014-0006938, but the range thereof is not limited thereto.

As used herein, the term "insulin analogue" means insulin having a modification of one or more amino acids in a natural (intact) sequence.

The insulin analogue may be an insulin analogue that has a variation of amino acids of the B or A chain of insulin, having reduced insulin titer and/or reduced insulin receptor binding ability compared to a natural type.

The insulin used in the present invention is an insulin analogue produced by genetic recombination technology, but the present invention is not limited thereto, and preferably includes inverted insulin, insulin variants, insulin fragments and the like. The production method may be performed through genetic recombination as well as a solid-phase method, but is not limited thereto.

The insulin analogue is a peptide that has the same in-vivo glycemic control function as insulin, which include insulin agonists, derivatives, fragments and variants and the like.

The insulin agonist of the present invention refers to a substance that binds to the in-vivo receptor of insulin and exhibits the same biological activity as insulin, regardless of the structure of insulin.

The insulin analogue of the present invention may be homologous to the A and B chains and the respective amino acid sequences of natural insulin and may have a variation selected from the group consisting of substitution (e.g., alpha-methylation, alpha-hydroxylation), removal (e.g., deamination), modification (e.g., N-methylation) and combinations thereof, and may mean a peptide having a function of controlling blood glucose in the body.

In the present invention, the insulin analogue may mean a peptide mimic and a low-molecular or high-molecular compound that is capable of binding to an insulin receptor and controlling blood glucose even though the amino acid sequence has no typical homology with natural insulin.

The insulin fragment of the present invention refers to an insulin form in which one or more amino acids are added to or deleted from insulin, and the added amino acid may be an amino acid (e.g., a D-type amino acid) which does not exist in a natural state, and such an insulin fragment may has a glycemic control function.

The insulin variant of the present invention means a peptide that has one or more amino acid sequences different from insulin and retains a blood glucose control function in the body.

The preparation methods each used in the insulin agonists, derivatives, fragments and variants of the present invention may be used independently and may be combined. For example, peptides that have one or more different amino acid sequences, are deaminated in amino-terminal amino acid residues and have a glycemic control function in the body are included.

Specifically, the insulin analogue may have a substitution of one or more amino acids selected from the group consisting of amino acids 1, 2, 3, 5, 8, 10, 12, 16, 23, 24, 25, 26, 27, 28, 29 and 30 of the chain B, and amino acids 1, 2, 5, 8, 10, 12, 14, 16, 17, 18, 19 and 21 of the chain A, with other amino acid, preferably with alanine, glutamate, asparagine, isoleucine, valine, glutamine, glycine, lysine, histidine, cysteine, phenylalanine, tryptophan, proline, serine, threonine, or aspartate. In addition, an insulin analogue having a deletion of one or more amino acids also falls within the scope of the present invention, but any insulin analogue may fall within the scope of the present invention without limitation.

Preferred insulin analogues are insulin analogues having an increased half-life compared to natural insulin, when combined with a biocompatible material or carrier, and such analogues may be the insulin analogues disclosed in Korean Patent Application Nos. 10-2014-0022909 and 10-2014-0006938, but are not limited thereto.

When albumin is used as a carrier in the composition of the present invention, the present invention may include, but is not limited to, techniques for directly covalently bonding albumin or albumin fragments to insulin and/or ATPIF1 to increase in vivo stability, techniques for binding albumin-binding substances, for example, albumin-specific binding antibodies or antibody fragments, to peptides, and binding the same to albumin, rather than directly binding albumin to the peptides, and techniques for binding specific peptides/proteins having albumin-binding ability to the peptides, including techniques for binding fatty acids having albumin-binding ability thereto, and may include any technique, binding method or the like that may increase in-vivo stability using albumin.

The present invention may also include techniques for binding to the peptides using an antibody or antibody fragment as a carrier to increase in vivo half-life. Such an antibody or antibody fragment may be an antibody or antibody fragment having an FcRn binding site, or may be any antibody fragment that does not include an FcRn binding site, such as Fab. The CovX-body technique of CovX Co., Ltd., which uses catalytic antibodies, may be included therein, and a technology for increasing half-life in vivo using Fc fragments may also fall within the scope of the present invention. When the Fc fragment is used, the linker for binding to the Fc fragment and peptides and the binding method thereof may be polyethylene glycol and a peptide bond, respectively, but are not limited thereto, and any chemical bonding method is possible. In addition, the binding ratio of the Fc fragment and the insulin in the present invention may be 1:1 or 1:2, but is not limited thereto.

Techniques for binding to insulin analogues using a peptide or protein fragment as a carrier to increase half-life in vivo may also fall within the scope of the present invention. The peptide or protein fragment used may be an elastin-like polypeptide (ELP) consisting of repeating units of a combination of specific amino acids. The present invention includes the technology of Xten, an artificial polypeptide PEG produced by Versartis Inc. The present invention also includes structure-inducing-probe (SIP) technology that increases the in vivo half-life using multi-lysine produced by Zealand Co., Ltd, CTP fusion technology of Prolor Corporation, and transferrin, which is known to have high stability in vivo, fibronectin, which is a component of connective tissue, and derivatives thereof.

Peptides or proteins that bind to ATPIF1 or insulin of the present invention are not limited thereto, and any peptide or protein that increases the in-vivo half-life of insulin falls within the scope of the present invention. In addition, the binding of the ATPIF1 or insulin of the present invention to a peptide or protein which increases the in vivo half-life may be a covalent bond, and the type and the binding method of the linker may be polyethylene glycol and a peptide bond, respectively, but are not necessarily limited thereto and any chemical bonding form is also possible.

In addition, the carrier used to increase the half-life in vivo may be a non-peptide substance such as polysaccharide or fatty acid. The linker that binds the carrier that can increase the in-vivo half-life of the peptide may include a peptide, polyethylene glycol, fatty acid, sugar, a high-molecular weight polymer, a low-molecular weight compound, nucleotide or a combination thereof, and any chemical bond, such as a non-covalent chemical bond or a covalent chemical bond, is possible, and there is no limitation as to the type of the chemical bond.

Preparations capable of increasing bioavailability or continuously sustaining activity may include sustained-release formulations based on microparticles, nanoparticles, and the like using PLGA, hyaluronic acid, chitosan, and the like.

In addition, other aspects of preparations that can increase bioavailability or maintain sustained activity may be preparations, such as implants, inhalations, transnasal preparations and patches.

In the present invention, examples of co-administrable insulin include natural insulin, insulin analogues, and long-acting insulins (e.g., Humulin and Novolin as natural insulins, Novolog, Humalog and Apidra as fast-acting insulins, and Lantus, Levemir and Tresiba as long-acting insulins).

Carrier substances that can be used in the present invention may be selected from the group consisting of antibodies, immunoglobulin Fc regions, albumin, fatty acids, carbohydrates, polymers having peptides as repeating units, transferrins and PEGs, preferably immunoglobulin Fc regions. In a specific embodiment of the invention, the sustained insulin or sustained GLP-1/glucagon dual agonist is linked to a carrier via a non-peptidyl polymer as a linker. In a more specific embodiment, the carrier linked to this non-peptidyl polymer linker is an immunoglobulin Fc fragment. The binding of the immunoglobulin Fc region to the insulin or dual agent may be in-frame fusion without any linker, or may be achieved using a non-peptidyl polymer as a linker. In the present invention, immunoglobulin Fc may be used interchangeably with an immunoglobulin fragment.

As used herein, the term "non-peptidyl polymer" means a biocompatible polymer having two or more repeating units bound together, and the repeating units are linked to one another through a covalent bond, rather than a peptide bond. In the present invention, the non-peptidyl polymer may be used interchangeably with a "non-peptidyl linker".

The non-peptidyl polymer that can be used in the present invention may be selected from the group consisting of biodegradable polymers such as polyethylene glycol, polypropylene glycol, copolymers of ethylene glycol and propylene glycol, polyoxyethylated polyols, polyvinyl alcohols, polysaccharides, dextran, polyvinyl ethyl ether, PLA (polylactic acid) and PLGA (polylactic-glycolic acid), lipid polymers, chitin, hyaluronic acid and combinations thereof, preferably polyethylene glycol. Derivatives thereof known in the art and derivatives that can be easily prepared at the technical level of the art fall within the scope of the present invention.

The peptidyl linker used for the fusion protein prepared by the conventional in-frame fusion method is disadvantageous in that it is easily cleaved by proteases in vivo, and thus the effect of increasing the half-life of the active drug by the carrier cannot be obtained as expected.

However, in the present invention, it is possible to maintain the half-life of the peptide in the blood, similarly to the carrier, using a protease-resistant polymer. Therefore, any non-peptidyl polymer can be used in the present invention without limitation as long as it is a polymer that performs the role described above, that is, is resistant to a protease in vivo.

The molecular weight of the non-peptidyl polymer ranges from 1 to 100 kDa, preferably from 1 to 20 kDa. In addition, the non-peptidyl polymer of the present invention, which is combined with the immunoglobulin Fc region, may be used not only as one kind of polymer but also as a combination of different kinds of polymers.

The non-peptidyl polymer used in the present invention may have a reactive group that can be combined with an immunoglobulin Fc region and a protein drug. Both terminal reactive groups of the non-peptidyl polymer are preferably selected from the group consisting of reactive aldehyde groups, propionic aldehyde groups, butyl aldehyde groups, maleimide groups and succinimide derivatives. Such a succinimide derivative may be succinimidyl propionate, hydroxy succinimidyl, succinimidyl carboxymethyl or succinimidyl carbonate. In particular, when the non-peptidyl polymer has, as a reactive group, an aldehyde reactive group at both ends, it is effective in minimizing non-specific reactions and in binding to biologically active polypeptides and immunoglobulins, respectively, at both ends of the non-peptidyl polymer. The final product obtained through reductive alkylation by aldehyde bonds is much more stable than those linked by amide bonds. The aldehyde reactive group selectively reacts with the N-terminus at low pH and can form a covalent bond with a lysine residue at high pH, for example, at pH 9.0. Both terminal reactive groups of the linker, which is the non-peptidyl polymer, may be the same as or different from each other. For example, a maleimide group may be present at one end, and an aldehyde group, a propionic aldehyde group or a butyl aldehyde group may be present at the other end. When polyethylene glycol having a hydroxyl reactive group at both ends is used as a non-peptidyl polymer, the hydroxyl group may be activated into one of the various reactive groups through a well-known chemical reaction, or long-acting insulin or insulin derivative conjugates of the present invention and long-acting GLP-1/glucagon conjugates may be prepared using commercially available modified polyethylene glycol having a reactive group.

In addition, the immunoglobulin Fc region is advantageous in terms of the preparation, purification and yield of the conjugate due to the relatively low molecular weight thereof compared to the whole immunoglobulin molecule and is expected to exhibit the effects of greatly increasing the homogeneity of the substance and reducing the possibility of inducing antigenicity in the blood due to the removal of the Fab moiety, which shows high heterogeneity, because the amino acid sequence differs from an antibody to an antibody.

As used herein, the term "immunoglobulin Fc region" means a heavy-chain constant region 2 (CH2) and a heavy-chain constant region 3 (CH3), excluding the heavy-chain and light-chain variable regions, the heavy-chain constant region 1 (CH1) and the light-chain constant region (CL1) of immunoglobulin, and may include a hinge domain in the heavy-chain constant region. In addition, the immunoglobulin Fc region of the present invention may be an expanded Fc region which includes all or part of a heavy-chain constant region (CH1) and/or a light-chain constant region (CL1), excluding the heavy- and light-chain variable regions of the immunoglobulin, as long as it has substantially the same effect as the natural type or an improved effect than the same. The immunoglobulin Fc region may also be a region from which some considerably long amino acid sequences corresponding to CH2 and/or CH3 have been removed. That is, the immunoglobulin Fc region of the present invention may be 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or two or more domains with an immunoglobulin hinge region (or a portion of the hinge region), or 6) a dimer of each domain of a heavy-chain constant region and a light-chain constant region.

In addition, the immunoglobulin Fc region of the present invention includes not only natural amino acid sequences but also sequence derivatives (mutants) thereof. Amino acid sequence derivatives mean that one or more amino acid residues in the natural amino acid sequence have different sequences due to deletion, insertion, non-conservative or conservative substitution, or a combination thereof. For example, for IgG Fc, amino acid residues 214 to 238, 297 to 299, 318 to 322 or 327 to 331, which are known to be important for binding, can be used as suitable sites for modification.

In addition, various kinds of derivatives, in which sites capable of forming disulfide bonds are removed, a few amino acids at the N-terminus are removed from the natural Fc, or methionine residues are added to the N-terminus of the natural Fc, are possible. In addition, the complement-binding sites, for example, C1q-binding sites or ADCC (antibody-dependent cell-mediated cytotoxicity) sites, may be removed in order to eliminate the effector function. Techniques for producing sequence derivatives of such immunoglobulin Fc regions are disclosed in PCT International WO 97/34631, WO 96/32478, and the like.

Amino acid exchanges in proteins and peptides that do not alter the activity of molecules as a whole are known in the art (H. Neurode, R. L. Hill, The Proteins, Academic Press, New York, 1979). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly. In some cases, modification such as phosphorylation, sulfation, acrylation, glycosylation, methylation, farnesylation, acetylation and amylation may be possible.

The above-described Fc derivatives are derivatives which exhibit the same biological activity as the Fc region of the present invention and have enhanced structural stability to heat, pH, etc. of the Fc region.

In addition, this Fc region may be obtained from a natural type separated in vivo from animals such as humans, cows, goats, pigs, mice, rabbits, hamsters, rats or guinea pigs, or may be a recombinant type or derivative thereof obtained from transformed animal cells or microorganisms. Here, the method of obtaining the same from the natural type may be a method including separating the whole immunoglobulin from a human or animal body and then treating the same with a protease. When treated with papain, the immunoglobulin is cleaved into Fab and Fc, and when treated with pepsin, the immunoglobulin is cleaved into pF'c and F(ab)2. Fc or pF'c may be separated using size-exclusion chromatography. Preferably, the Fc region is a recombinant immunoglobulin Fc region in which a human-derived Fc region is obtained from a microorganism.

In addition, the immunoglobulin Fc region may take the form of a native sugar chain, a sugar chain increased (longer) compared to the native form, a sugar chain decreased (shorter) compared to the native form, or a form in which a sugar chain is removed from the native form. The increase or decrease, or removal of the sugar chain can be performed by a conventional method known in the art such as a chemical method, an enzymatic method, and a genetic-engineering method using microorganisms. Herein, the immunoglobulin Fc region in which the sugar chain is removed from the Fc has significantly reduced binding strength with the complement (c1q), and has reduced or eliminated antibody-dependent cytotoxicity or complement-dependent cytotoxicity, thus causing no undesired immune response in vivo. In this regard, a form that is further consistent with the original function as a carrier of a drug may be considered to be a deglycosylated or aglycosylated immunoglobulin Fc region.

As used herein, the term "deglycosylation" refers to an Fc region, from which sugar is removed by an enzyme, and the term "aglycosylation" refers to an Fc region that is produced and is not glycosylated in a prokaryotic animal, preferably E. coli.

Meanwhile, the immunoglobulin Fc region may originate from humans or animals such as cattle, goats, pigs, mice, rabbits, hamsters, rats or guinea pigs, preferably humans.

In addition, the immunoglobulin Fc region may be an Fc region derived from IgG, IgA, IgD, IgE, IgM, or a combination thereof or a hybrid thereof. The immunoglobulin Fc region is preferably derived from IgG or IgM, which is most abundant in human blood and is most preferably derived from IgG, which is known to enhance the half-life of ligand-binding proteins.

Meanwhile, as used herein, the term "combination" means, when forming a dimer or multimer, that a polypeptide encoding a single-chain immunoglobulin Fc region having the same origin forms a bond with a single-chain polypeptide having a different origin. That is, it is possible to prepare dimers or multimers from two or more fragments selected from the group consisting of IgG Fc, IgA Fc, IgM Fc, IgD Fc and IgE Fc fragments.

As used herein, the term "hybrid" means that sequences corresponding to two or more different origins of immunoglobulin FC fragments are present in a single-chain immunoglobulin FC domain. In the present invention, a variety of hybrid forms are possible. That is, domain hybrids including one to four domains selected from the group consisting of CH1, CH2, CH3 and CH4 of IgG Fc, IgM Fc, IgA Fc, IgE Fc and IgD Fc are possible, and may include hinges.

Meanwhile, IgG may also be divided into IgG subtypes, i.e., IgG1, IgG2, IgG3 and IgG4, and in the present invention, a combination thereof or a hybrid thereof is also possible. Preferred are IgG2 and IgG4 subclasses, and most preferred is an Fc region of IgG4 having almost no effector function, such as complement-dependent cytotoxicity (CDC).

That is, the most preferred immunoglobulin Fc region for a carrier of a drug of the present invention is an aglycosylated Fc region derived from human IgG4. The human-derived Fc region is more preferable than a non-human-derived Fc region that may cause undesirable immune responses, for example, acting as antigens in humans in vivo to produce new antibodies thereto.

The method for producing sustained insulin conjugates of the present invention is not particularly limited. The description relating to examples of detailed production methods and the effects thereof are found in, for example, Korean Patent Nos. 10-1330868 and 10-1324828 and 10-1058290, Korean Patent Laid-open No. 10-2011-0111267 and Korean Patent Application No. 10-2014-0022909.

When ATPIF1 and insulin of the present invention are co-administered, the ATPIF1 and insulin act simultaneously to reduce the concentration of glucose in the blood and show stable changes, compared to when either ATPIF1 or insulin is administered alone. In addition, when the conjugate is administered in combination, it is possible to reduce the risk of hypoglycemia that may occur when insulin is administered alone, to reduce body weight and to lower the total insulin dose by the insulin-secreting peptide. The administration of the combination of ATPIF1 and insulin has a great advantage in improving the quality of life of patients by reducing the frequency of administration to chronic patients, who have conventionally required daily administration, due to the dramatic increase in blood half-life and sustained in-vivo effects. In addition, the pharmaceutical composition of the present invention has excellent in-vivo sustainability and titer and can significantly reduce the dose using a combination administration method.

ATPIF1 and insulin may be administered simultaneously, sequentially or in reverse order, and may be administered simultaneously in a combination of appropriate effective amounts. In addition, preferably, ATPIF1 and insulin may be co-administered simultaneously, sequentially or in reverse order after being stored in separate containers.

In addition, the compositions for the combined administration of the present invention, the sustained insulin conjugate and the sustained GLP-1/glucagon dual agonist conjugate may be provided as a kit for treating diabetes contained in one container, or a kit for treating diabetes, each stored in separate containers. Such a kit may include a pharmaceutically acceptable carrier and an instruction for use of the kit.

In addition, the present invention identified that ATPIF1 (ATPase inhibitor factor 1), the protein, which plays a role in inhibiting ATP synthesis in mitochondria, functions to control glucose in muscle cells and fat metabolism in adipocytes.

Obesity is caused by the accumulation of fat triglycerides (TGs) in adipocytes through adipogenesis, and controlling this adipogenesis is a known effective treatment for obesity inhibition (Chen, H. C. and Farese, R. V. Arterioscler. Thromb. Vasc. Biol. 25,482-4865,2005; Cooke, D. and Bloom, S., Nat. Rev. Drug Discov. 5, 919-1200, 2006).

The present invention identified that ATIF1 controls ACC activity involved in the inhibition of fat synthesis in adipocytes and is involved in improvement of fat metabolism by increasing the expression of UCP1, which is a browning marker. Animal experiments were conducted to determine whether or not the concentration of myokine ATIF1 was high in animals performing exercise, and the result showed that the concentration of ATIF1 in the exercise group increased.

In another aspect, the present invention is directed to a pharmaceutical composition for preventing or treating obesity containing ATPIF1 (ATPase inhibitor factor 1) as an active ingredient.

In another aspect, the present invention is directed to a method of preventing or treating obesity using ATPIF1 (ATPase inhibitor factor 1).

In another aspect, the present invention is directed to a use of ATPIF1 (ATPase inhibitor factor 1) for prevention or treatment of obesity.

In another aspect, the present invention is directed to a use of ATPIF1 (ATPase inhibitor factor 1) for manufacturing medicament for treating or preventing obesity.

The composition of the present invention may be used in combination with a variety of therapeutic agents that are effective for treating such diseases or problems. As can be clearly described above, current diabetes treatments include dietary control, exercise, insulin, insulin secretagogues, glucose-reducing agonists, PPAR-γ agonists and alpha-glucosidase inhibitors. The compound of the present invention may be used in combination with such or other medical treatments to treat and/or prevent diabetes and related disorders, including, but not limited to, other symptoms such as type I diabetes, type II diabetes, obesity, glucose intolerance, insulin resistance, metabolic syndrome, hyperlipidemia, hypercholesterolemia, atherosclerosis, neurodegenerative diseases, inflammation and stroke. For example, when treating type II diabetes, the compound of the present invention may be used in combination of one or more pharmaceutically effective drugs including sulfonylureas such as metformin, glyburide and glipizide, thiazolidinediones such as repaglinide, nateglinide, rosiglitazone and pioglitazone, acarbose, miglitol, exenatide, pramlintide and insulin.

The therapeutic composition according to the present invention may further contain a pharmaceutically acceptable carrier, and the pharmaceutically acceptable carrier includes a carrier, an adjuvant and a vehicle, which are collectively referred to as "pharmaceutically acceptable carriers". The pharmaceutically acceptable carrier that can be used for the pharmaceutical composition of the present invention may include, but is not limited to, ion exchange resins, alumina, aluminum stearate, lecithin, serum proteins (e.g., human serum albumin), buffer substances (e.g., partial glyceride mixtures of several phosphates, glycine, sorbic acid, potassium sorbate and saturated vegetable fatty acids), water, salts or electrolytes (e.g., protamine sulfate, disodium hydrogen phosphate, potassium hydrogen phosphate, sodium chloride and zinc salts), colloidal silica, magnesium trisilicate, polyvinyl pyrrolidone, cellulose-based substrates, polyethylene glycols, sodium carboxymethylcellulose, polyarylates, waxes, polyethylene-polyoxypropylene-blocking polymers, polyethylene glycols, wool and the like.

The route of administration of the pharmaceutical composition according to the present invention includes, but is not limited to, oral, intravenous, intramuscular, intraarterial, intramedullary, intradural, intracardiac, transdermal, subcutaneous, intraperitoneal, intranasal, intestinal, topical, sublingual or rectal administration. As used herein, the term "parenteral" includes subcutaneous, intradermal, intravenous, intramuscular, intraarticular, intrabursal, intrasternal, intradural, intralesional and intracranial injection or infusion techniques.

The pharmaceutical composition may be in the form of a sterile injectable preparation as a sterile injectable aqueous or oily suspension. This suspension may be formulated according to techniques known in the art using a suitable dispersing or wetting agent (e.g., Tween 80) and a suspending agent. The sterile injectable preparation may also be a sterile injectable solution or suspension (e.g., a solution in 1,3-butanediol) in a nontoxic parenterally acceptable diluent or solvent. Available acceptable vehicles and solvents may include mannitol, water, Ringer's solution and isotonic sodium chloride solutions. In addition, sterile nonvolatile oils are commonly used as solvents or suspending media. For this purpose, any less irritating oil containing synthetic mono- or di-glycerides may also be used. Fatty acids such as oleic acid and glyceride derivatives thereof are useful for injectable preparations, like pharmaceutically acceptable natural oils (e.g., olive oil or castor oil), particularly polyoxyethylated forms thereof.

The pharmaceutical composition of the present invention may be administered orally in any orally acceptable dosage form including, but not limited to, capsules, tablets, and aqueous suspensions and solutions. For oral tablets, commonly used carriers include lactose and corn starch. Lubricants such as magnesium stearate are also typically added. Useful diluents for oral administration in a capsule form include lactose and dried corn starch. When the aqueous suspension is administered orally, the active ingredient is combined with an emulsifier and a suspending agent. If necessary, a sweetening agent, a flavoring agent and/or a coloring agent may be added.

The pharmaceutical compositions of the present invention may also be administered in the form of a suppository for rectal administration. These compositions can be prepared by mixing the compound of the present invention with suitable non-irritating excipients which are solid at room temperature but liquid at a rectal temperature. Such materials include, but are not limited to, cocoa butter, beeswax and polyethylene glycols.

Oral administration of the pharmaceutical composition according to the present invention is particularly useful when the desired treatment relates to a site or organ that is easily accessible by topical application. When applied topically to the skin, the pharmaceutical composition should be formulated in a suitable ointment containing the active ingredient suspended or dissolved in a carrier. The carrier for topical administration of the compound of the present invention includes, but is not limited to, mineral oil, liquid paraffin, white petrolatum, propylene glycol, polyoxyethylene, polyoxypropylene compounds, emulsifying wax and water. Alternatively, the pharmaceutical composition may be formulated in a suitable lotion or cream containing the active compound suspended or dissolved in a carrier. The suitable carrier includes, but is not limited to, mineral oil, sorbitan monostearate, polysorbate 60, cetyl ester wax, cetearyl alcohol, 2-octyldodecanol, benzyl alcohol and water. The pharmaceutical composition of the invention can also be applied topically in the form of a rectal suppository or suitable enema to the lower intestine. Topically applied transdermal patches also fall within the scope of the present invention.

The pharmaceutical composition of the present invention can be administered by nasal aerosol or inhalation. Such a composition is prepared according to techniques well-known in the pharmaceutical field and is prepared as a solution in saline using benzyl alcohol or other suitable preservatives, absorption accelerators to enhance bioavailability, fluorocarbon and/or other solubilizers or dispersants known in the art.

The composition of the present invention can be used in combination with a conventional anti-inflammatory agent or in combination with a matrix metalloprotease inhibitor, a lipoxygenase inhibitor and an inhibitor of cytokine other than IL-1β. The composition of the present invention may be administered in combination with an immunomodulator (e.g., bropirimine, anti-human alpha interferon antibody, IL-2, GM-CSF, methionine enkephalin, interferon-alpha, diethyldithiocarbamate, tumor necrosis factor, naltrexone and rEPO) or prostaglandin to prevent or eliminate symptoms of IL-1-mediated disease such as inflammation. When the composition of the present invention is administered in combination with other therapeutic agents, it may be administered sequentially or simultaneously therewith to the patient. Alternatively, the pharmaceutical composition according to the present invention may be prepared by mixing ATPIF1 with other therapeutic or prophylactic agents described above.

As used herein, the term "therapeutically effective amount" refers to a dose level of about 0.1 mg to about 100 mg per kg of body weight per day for use in the treatment of the symptom described above.

However, it will be understood that a particular effective amount for a particular patient may vary depending on a variety of factors including the activity of the specific compound used, age, weight, general health, gender, diet, time of administration, route of administration, excretion rate, drug combination and severity of the certain disease to be prevented or treated. The pharmaceutical composition according to the present invention may be formulated into a pill, dragée, capsule, solution, gel, syrup, slurry or suspension.

In a preferred embodiment, the pharmaceutical composition for oral administration can be prepared by mixing the active ingredient with a solid excipient and can be prepared in the form of a granule to obtain a tablet or dragée formulation. Suitable excipients include sugar forms such as lactose, sucrose, mannitol and sorbitol, starch from corn, flour, rice, potatoes or other plants, or cellulose such as methyl cellulose, hydroxypropylmethyl-cellulose or sodium carboxymethylcellulose, carbohydrates such as gums, including arabic gum and tragacanth gum, or protein fillers such as gelatin and collagen. If necessary, a disintegrant or solubilizer, such as crosslinked polyvinylpyrrolidone, agar and alginic acid or a salt form thereof, for example, sodium alginate, may be added.

In a preferred embodiment, for parenteral administration, the pharmaceutical composition of the present invention may be prepared in an aqueous solution. Preferably, a physically suitable buffer such as Hanks' solution, Ringer's solution, or physically buffered saline may be used. Aqueous injection suspensions may be added with a substrate that can increase the viscosity of the suspension, such as sodium carboxymethyl cellulose, sorbitol or dextran. In addition, the suspension of the active ingredient may be prepared as a suitable oily injection suspension. Suitable lipophilic solvents or carriers include fatty acids such as sesame oil or synthetic fatty acid esters such as ethyl oleate, triglycerides or liposomes. Non-lipid polycationic amino polymers may also be used as carriers. Optionally, the suspension may use a suitable stabilizer or agent to increase the solubility of the compound and to prepare a highly concentrated solution.

EXAMPLE

Hereinafter, the present invention will be described in more detail with reference to examples. However, it will be obvious to those skilled in the art that these examples are suggested only for illustration of the present invention and should not be construed as limiting the scope of the present invention.

Example 1: Identification of Increased AMPK Phosphorylation in Muscle Cell Line by ATPIF1

In order to determine the effect of ATPIF1 on phosphorylation of AMPK (AMP-activated protein kinase) in muscle cells, the muscle cell line (ATCC C2C12) was cultured on a 12-well plate in DMEM (10% FBS) medium containing 5% FBS for 24 hours and was then treated with ATPIF1 (Phoenix Pharmaceuticals, Burlingame, Calif., USA) at different times at different concentrations (0 ng/ml, 6 ng/ml, 20 ng/ml, 60 ng/ml, 200 ng/ml and 600 ng/ml). 30 μg of a cytoplasmic protein was subjected to electrophoresis on a 10% SDS-PAGE gel, followed by Western blotting analysis using AMPK (AMP-activated protein kinase) phosphorylated antibody (Millipore-Upstate, Billerica, Mass., USA).

Figure 1:
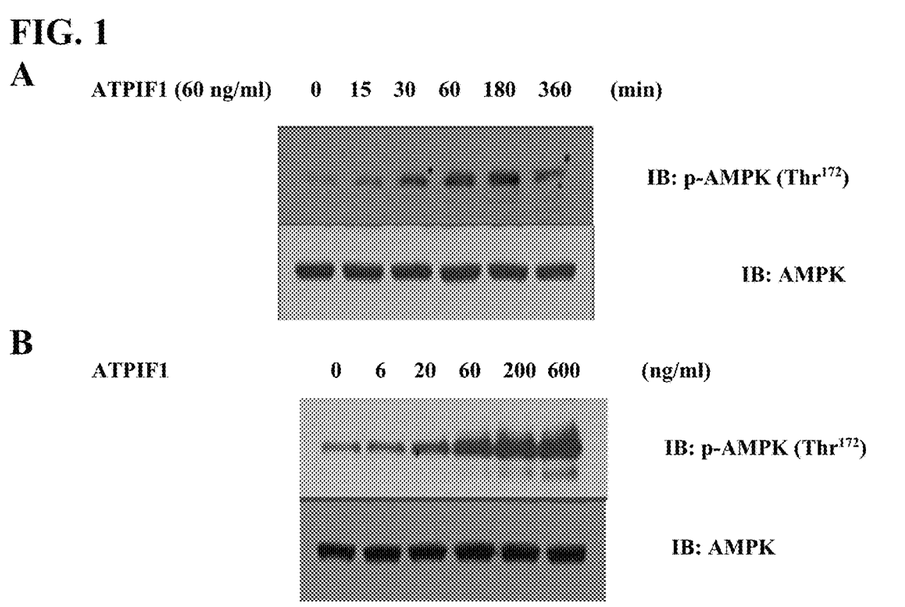
FIGS. 1A and 1B show Western blot results showing the increase in AMPK phosphorylation due to ATPIF1 in C2C12 skeletal muscle cell lines, with FIG. 1A showing that AMPK phosphorylation was maximized by treatment with ATPIF1 (60 ng/ml) for 1 to 3 hours, and FIG. 1B showing maximum effects to be obtained at 60 ng/ml of ATPIF1.

The result showed that, when treated with ATPIF1 (60 ng/ml) for 1 to 3 hours, AMPK phosphorylation was maximized (FIG. 1 in part A). In addition, when treated with ATPIF1 at different concentrations of 0 ng/ml, 6 ng/ml, 20 ng/ml, 60 ng/ml, 200 ng/ml and 600 ng/ml, AMPK phosphorylation began to increase at 20 ng/ml of ATPIF1, and the maximum effects were obtained at 60 ng/ml of ATPIF1 (FIG. 1 in part B). The total AMPK protein level was determined using an inactive AMPK antibody (Millipore-Upstate, Billerica, Mass., USA).

Example 2: Identification of Increased Akt Phosphorylation in Muscle Cell Line by ATPIF1

Akt is a main protein involved in glycemic control, along with AMPK. In order to determine the effect of ATPIF1 on phosphorylation of Akt in muscle cells, the muscle cell line (C2C12) cultured under the same conditions as Example 1 was treated with ATPIF1 at different times at different concentrations. Then, 30 μg of a cytoplasmic protein was subjected to electrophoresis on a 10% SDS-PAGE gel, followed by Western blotting analysis using Akt phosphorylated antibody (Millipore-Upstate, Billerica, Mass., USA).

Figure 2:
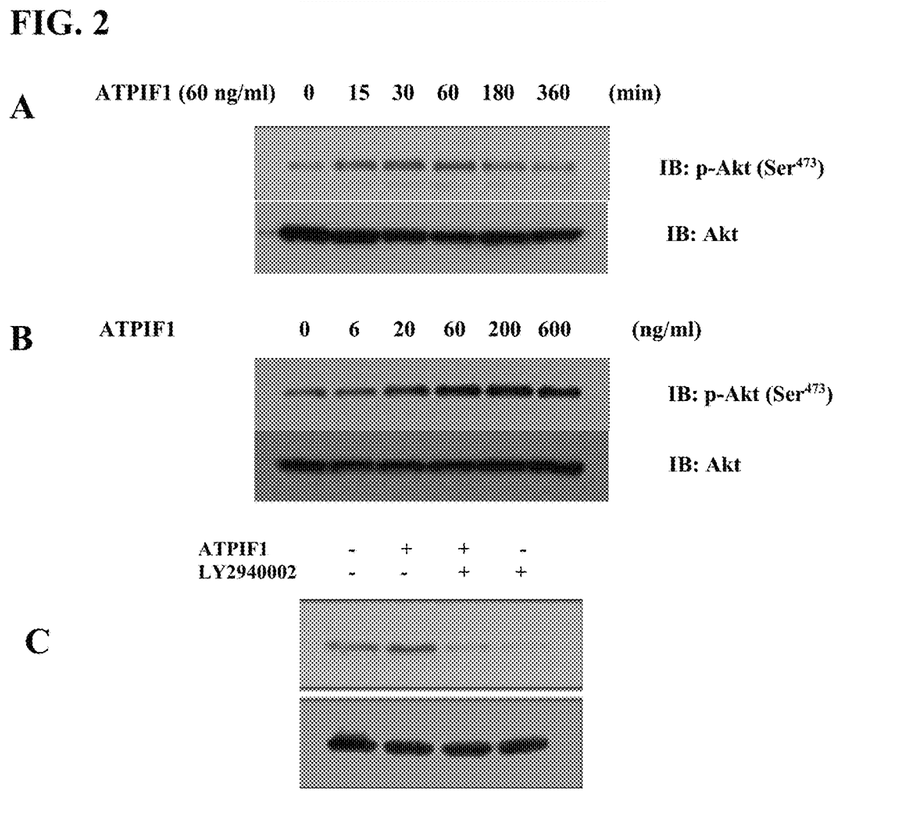
FIGS. 2A, 2B, and 2C show Western blot results showing the increase in Akt phosphorylation due to ATPIF1 in muscle cell lines, with FIG. 2A showing that Akt phosphorylation was maximized 3 hours after treatment with ATPIF1 (60 ng/ml), with FIG. 2B showing maximum effects obtained upon treatment at 60 ng/ml of ATPIF1, and with FIG. 2C showing that treatment with LY294002 inhibiting PI3K, an Akt upstream substance, eliminated the increase in Akt phosphorylation by ATPIF1, indicating that PI3K is involved in Akt phosphorylation by ATPIF1.

The results showed that, 3 hours after treatment with ATPIF1 (60 ng/ml), Akt phosphorylation was maximized (FIG. 2 in part A). In addition, when treated with ATPIF1 at different concentrations of 0 ng/ml, 6 ng/ml, 20 ng/ml, 60 ng/ml, 200 ng/ml and 600 ng/ml, Akt phosphorylation began to increase upon treatment at 20 ng/ml, and the maximum effects were obtained upon treatment at 60 ng/ml of ATPIF1 (FIG. 2 in part B).

In addition, the results showed that treatment with LY294002 (Calbiochem, San Diego, Calif., USA), which is an inhibitor of PI3K, an Akt upstream substance, eliminated the increase in Akt phosphorylation by ATPIF1, which indicates that PI3K is involved in Akt phosphorylation by ATPIF1 (FIG. 2 in part C). The total Akt protein level was determined using an inactive Akt antibody (Millipore-Upstate, Billerica, Mass., USA).

Example 3: Identification of Increased Glut4 Protein Expression in Muscle Cell Line by ATPIF1

The transporter plays a key role in transporting sugars into cells. In muscle cells, Glut4 plays a key role as a transporter. In order to determine whether or not the increases in AMPK phosphorylation and Akt phosphorylation caused by ATPIF1 actually improve Glut4 expression, the change of the expression of Glut4 in muscle cells by ATPIF1 treatment was analyzed through Western blotting using a glut4 antibody (Millipore-Upstate, Billerica, Mass., USA).

Figure 3:
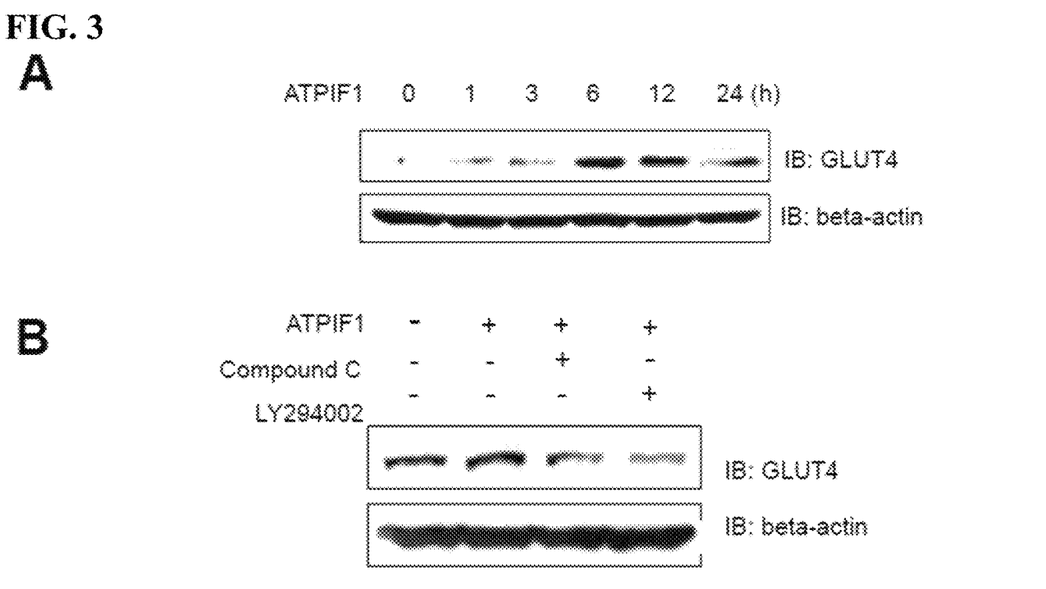
FIGS. 3A and 3B show Western blot results showing the increase in expression of Glut4 proteins due to ATPIF1 in muscle cell lines, with FIG. 3A showing Glut4 expression in muscle cells increased by treatment with ATPIF1, and with FIG. 3B showing that treatment with LY294002 inhibiting PI3K, and with compound C inhibiting AMPK, eliminated increase in GTP4 expression by ATPIF1, indicating that PI3K and AMPK are involved in Glut4 protein expression.

As a result, as can be seen from FIG. 3 in part A, Glut4 expression in muscle cells was increased by treatment with ATPIF1.

In addition, treatment with LY294002 (Calbiochem, San Diego, Calif., USA), which is an inhibitor of PI3K, and compound C (Calbiochem, San Diego, Calif., USA), which is an inhibitor of AMPK, eliminated the increase in GTP4 expression by ATPIF1, which indicates that PI3K and AMPK were found to be involved in Glut4 protein expression (FIG. 3 in part B). The beta-actin antibody (Millipore-Upstate, Billerica, Mass., USA) was used in order to determine the identity of the amount of protein used in the experiment.

Example 4: Identification of Increased Glut4 mRNA Expression in Muscle Cell Line by ATPIF1

RT-PCR analysis was performed to determine whether or not the change of the expression of glut4 protein by ATPIF1 occurred at the mRNA level as well.

Total RNA was isolated from the muscle cell line (C2C12) using TRI reagents (Life Technologies, UK). cDNA was synthesized from 1 µg of isolated RNA using a Thermoscript II one-step RT-PCR Kit (Life Technologies, UK). The cDNA was amplified using a Gene Amp System 9700 thermocycler (Applied Biosystems, UK), and PCR reaction was performed for 34 cycles (at 94° C. for 30 seconds, at 55° C. for 30 seconds, and at 72° C. for 60 seconds), followed by extension at 72° C. for 10 minutes.

The following primer pairs were used as primers.

GLUT4-sense: 5'-TTG GAG AGA GAG CGT CCA AT-3' (SEQ ID NO: 2)

GLUT4-antisense: 5'-CTC AAA GAA GGC CAC AAA GC-3'(SEQ ID NO: 3)

β-actin-sense: 5'-CAG GAG GAG CAA TGA TCT TGA-3'(SEQ ID NO: 4)

β-actin-antisense: 5'-ACT ACC TCA TGA AGA TCC TCA-3'(SEQ ID NO: 5)

10 µL of the RT-PCR reaction product obtained above was identified by electrophoresis on an agarose gel.

Figure 4:
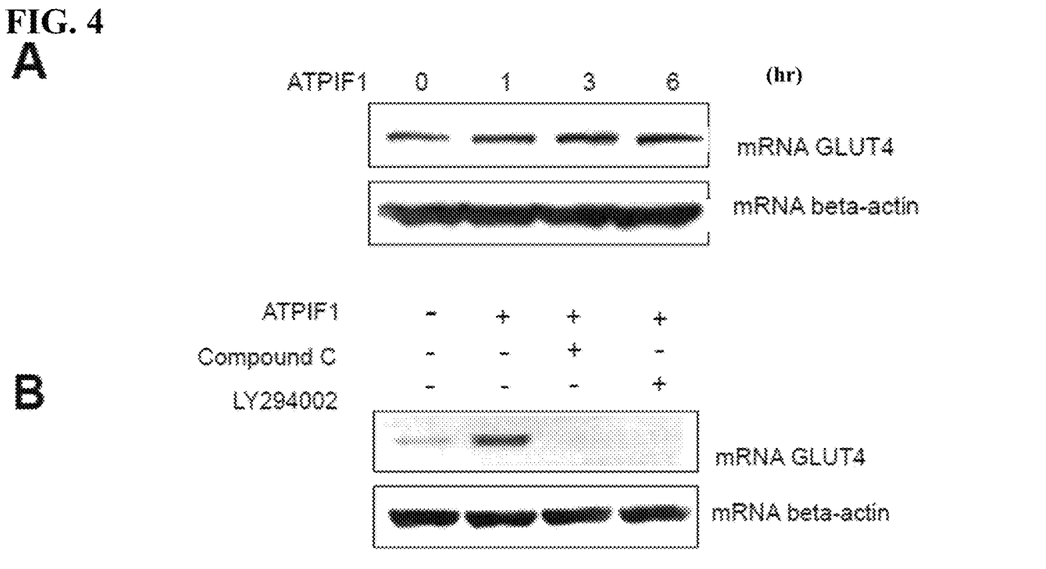
FIGS. 4A and 4B show Western blot results showing the increase in expression of Glut4 mRNAs due to ATPIF1 in muscle cell lines, with FIG. 4A showing Glut4 mRNA expression in muscle cells increased by treatment with ATPIF1, and with FIG. 4B showing that treatment with LY294002 inhibiting PI3K, and with compound C inhibiting AMPK, eliminated increase in GTP4 mRNA expression by ATPIF1, indicating that PI3K and AMPK are involved in Glut4 mRNA expression.

As a result, as can be seen from FIG. 4 in part A, Glut4 mRNA expression in muscle cells was increased by treatment with ATPIF1.

In addition, the treatment with LY294002 (Calbiochem, San Diego, Calif., USA), which is an inhibitor of PI3K, and compound C (Calbiochem, San Diego, Calif., USA), which is an inhibitor of AMPK, eliminated the increase in Glut4 mRNA expression by ATPIF1, which indicates that PI3K and AMPK were found to be involved in Glut4 mRNA expression (B). The beta-actin antibody was identified in order to determine the identity of the total mRNA.

Example 5: Identification of Increased Glucose Uptake in Muscle Cell Line by ATPIF1

The main feature of the glycemic control mechanism is the uptake (ingestion) of glucose into the cells.

In order to identify whether or not the increase in AMPK activity caused by ATPIF1 actually caused an increase in glucose uptake, an experiment was performed to determine whether or not glucose uptake into muscle cells actually occurred using isotopically labeled glucose.

Figure 5:
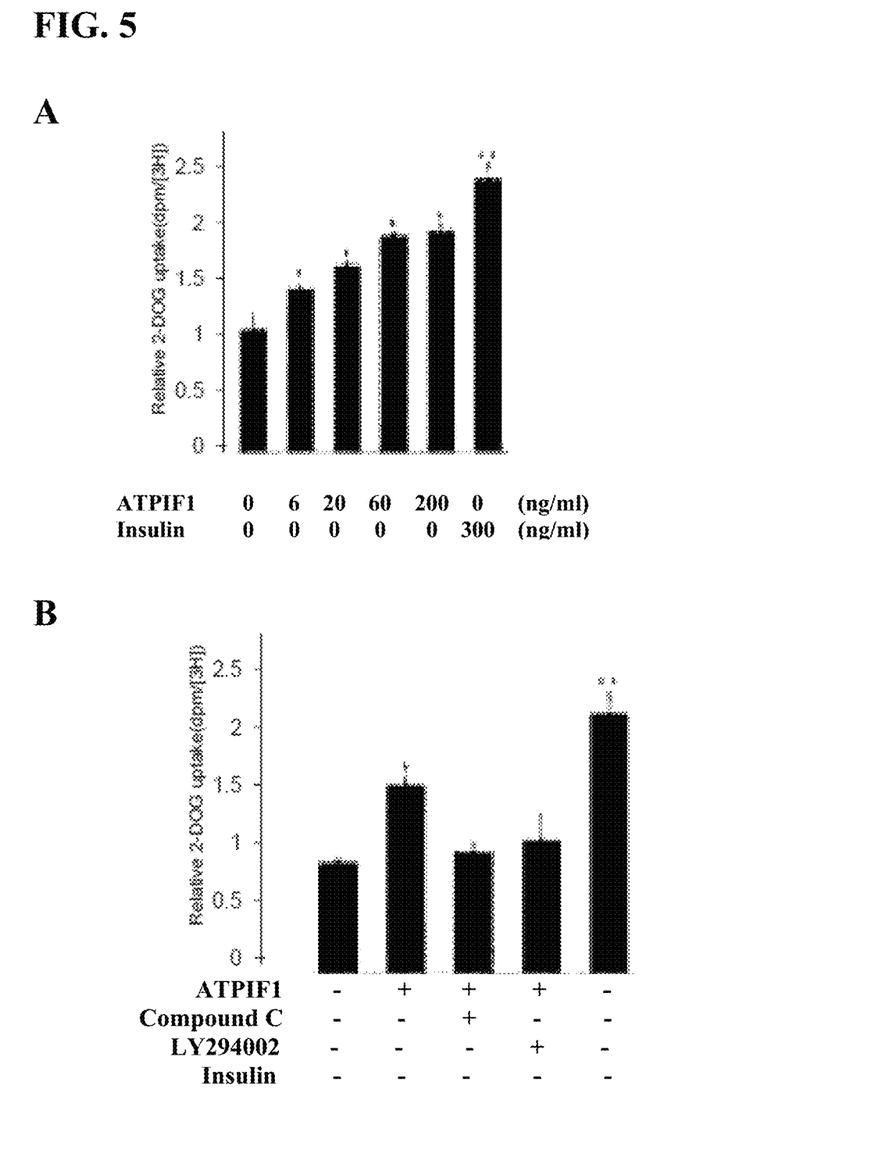

As a result, as can be seen from FIG. 5 in part A, the glucose uptake of muscle cells was increased by ATPIF1.

In addition, as can be seen from FIG. 5 in part B, when treated with LY294002, which is an inhibitor of PI3K, and compound C, which is an inhibitor of AMPK, along with ATPIF1, the increase in glucose uptake by ATPIF1 was eliminated, which indicates that PI3K and AMPK were involved in the glucose uptake process. Insulin (Sigma, St. Louis, Mo., USA) was used as a positive control.

Example 6: Identification of Insulin Sensitizer Function of ATPIF1 in Muscle Cell Line Most people with type 2 diabetes exhibit insulin resistance, which is the biggest obstacle to treatment. In order to overcome this, it is necessary to develop an insulin sensitizer for providing sensitivity to an insulin response. The sugar uptake experiments showed whether or not ATPIF1, which increases AMPK and Akt activity, can function as an insulin sensitizer.

Figure 6:
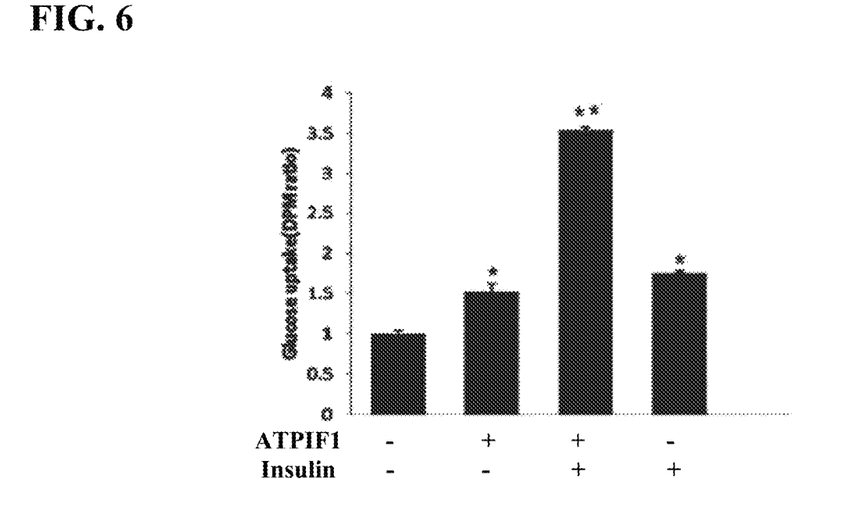
FIG. 6 shows Western blot results showing the function as an insulin sensitizer of ATPIF1 in muscle cell lines.

As a result, as can be seen from FIG. 6, compared to when treated with either insulin or ATPIF1 alone, when treated with a combination of ATPIF1 and insulin, the glucose uptake by insulin was further increased, which indicates that ATPIF1 functions as an insulin sensitizer.

Example 7: Determination of Inhibition of Fat Synthesis and Promotion of Browning by ATPIF1 in Adipocytes In order to determine whether or not ATPIF1 is capable of controlling obesity, whether or not ATPIF1 regulates the phosphorylation of ACC, which is a lipogenesis control protein, was identified.

Western blotting experiments were performed using an ACC phosphorylated antibody (Millipore-Upstate, Billerica, Mass., USA) in an adipocyte line (3T3L1) (ATCC: American Type Culture Collection) in DMEM (10% FBS) medium.

Figure 7:
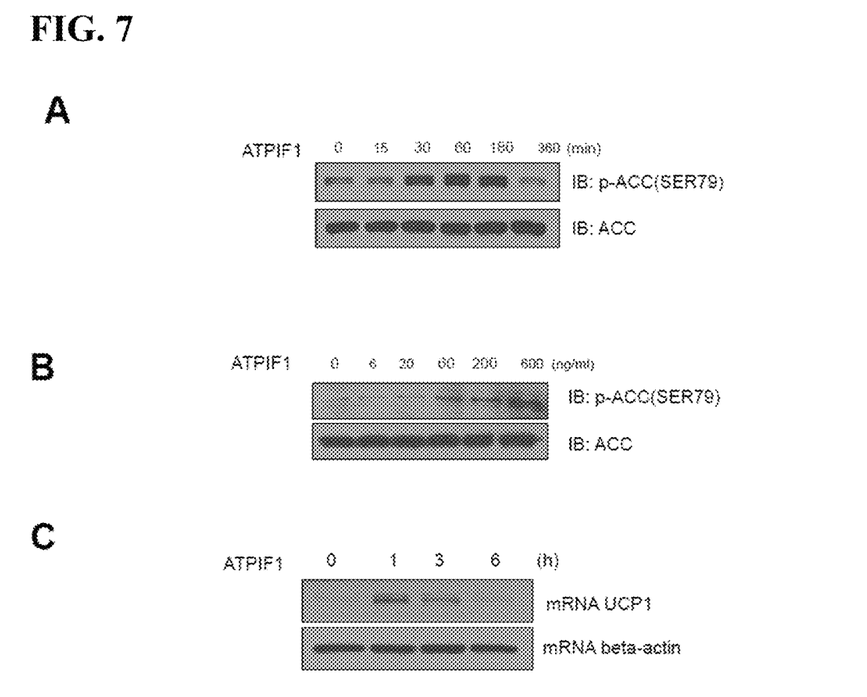
FIGS. 7A, 7B, and 7C show Western blot results showing ACC phosphorylation and UCP1 activation of ATPIF1 in adipocytes, with FIG. 7A showing ACC phosphorylation maximized after 30 minutes and 1 hour after treatment with ATPIF1, with FIG. 7B showing maximum effects obtained at a concentration of 60 ng/ml, and with FIG. 7C showing that treatment with ATPIF1 resulted in an increase in mRNA expression indicating that ATPIF1 has a function of inhibiting fat synthesis as well as a function of promoting browning of fat.

As a result, as can be seen from FIG. 7 in part A, 30 minutes and 1 hour after treatment with ATPIF1, ACC phosphorylation was maximized. As can be seen from FIG. in part B, when treated with ATPIF1 at different concentrations of 0 ng/ml, 6 ng/ml, 20 ng/ml, 60 ng/ml, 200 ng/ml and 600 ng/ml, ACC phosphorylation began to increase at a concentration of 20 ng/ml, and the maximum effects were obtained at a concentration of 60 ng/ml.

Total RNA was isolated from the muscle cell line (3T3L1) using the TRI reagent (Life Technologies, UK). cDNA was synthesized from 1 µg of isolated RNA using a Thermoscript II one-step RT-PCR Kit (Life Technologies, UK). The cDNA was amplified using a Gene Amp System 9700 thermocycler (Applied Biosystems, UK), and PCR reaction was performed for 34 cycles (at 94° C. for 30 seconds, at 55° C. for 30 seconds, and at 72° C. for 60 seconds), followed by extension at 72° C. for 10 minutes.

The following primer pairs were used as primers.

```
UCP1-sense:
                                    (SEQ ID NO: 6)
CTG CCT CTC TCG GAA ACA AG UCP1-antisense:
                                    (SEQ ID NO: 7)
GCC ACA AAC CCT TTG AAA AA β-actin-sense:
                                    (SEQ ID NO: 4)
5'-CAG GAG GAG CAA TGA TCT TGA-3'

β-actin-antisense:
                                    (SEQ ID NO: 5)
5'-ACT ACC TCA TGA AGA TCC TCA-3'
```

10 µL of the RT-PCR reaction product obtained above was identified by electrophoresis on an agarose gel.

As a result, the result of RT-PCR experiments on the change of the expression of UCP1, which is a browning marker gene in adipocytes, showed that treatment with ATPIF1 resulted in an increase in mRNA expression (FIG. 7 in part C), which indicates that ATPIF1 has a function of inhibiting fat synthesis as well as a function of promoting browning of fat.

Obesity is caused by the accumulation of intracellular triglycerides (TGs) of adipocytes through adipogenesis. Controlling this adipogenesis is known as an effective treatment for inhibition of obesity (Chen, H. C. and Farese, R. V. Arterioscler. Thromb. Vasc. Biol. 25,482-4865,2005; Cooke, D. and Bloom, S., Nat. Rev. Drug. Discov. 5, 919-1200, 2006), because brown fat cells are effective in the treatment of obesity and diabetes by heat generation (Aaron M Cyess and C Ronald Kanh, *Curr. Opin. Endocrinol. Diabetes Obes.*, 17:143, 2010). The results indicate that ATPIF1 has a therapeutic effect on obesity.

Example 8: Analysis of Concentration of ATPIF1 in Blood of Mice that Performed Exercise In order to determine the physiological significance of ATPIF1, whether or not the concentration of ATPIF1 was increased in the blood of animals that had performed exercise was identified.

10 mice (BALB/c, Central Lab Animal Inc., CLA) were prepared per group and the concentration of ATIF1 in the blood of a mouse (A) that had performed short-term exercise (collection of blood after exercise for an hour) and long-term exercise (collection of blood after exercise for an hour per day, over a month in total) was measured using an ELIZA kit (Myobiosource, San Diego, Calif., USA).

Figure 8:
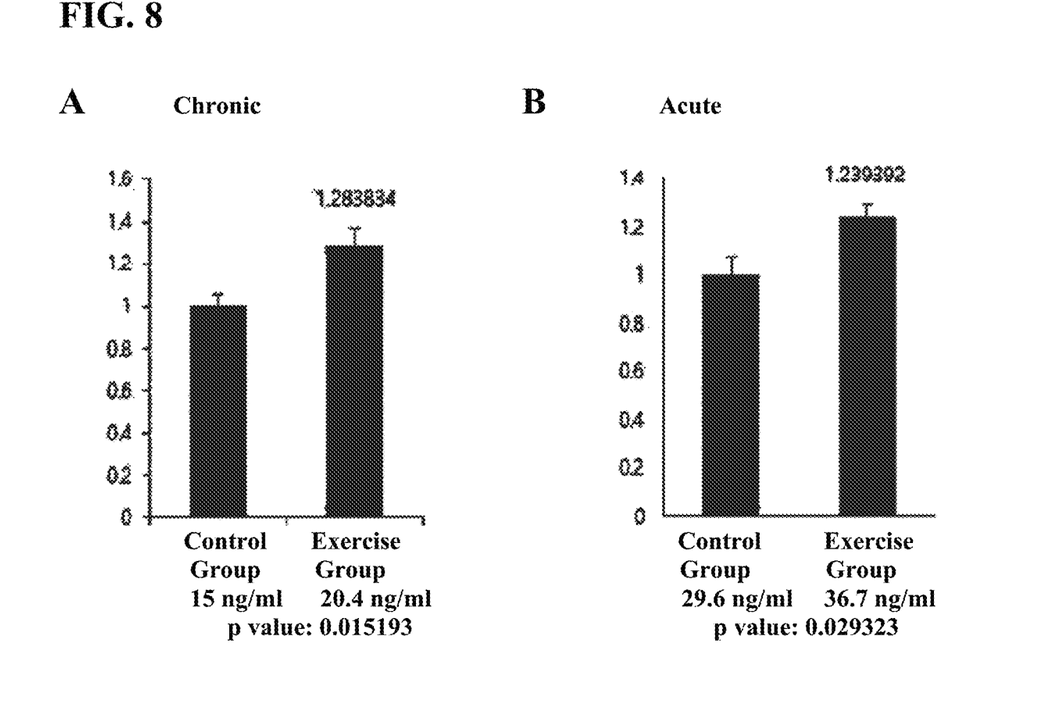
FIGS. 8A and 8B show results showing a change in the concentration of ATPIF1 in the blood during the motion of a mouse, with FIG. 8A showing concentration of ATPIF1 in the blood of a mouse that had performed short-term exercise for an hour, and with FIG. 8B showing concentration of ATPIF1 in the blood of a mouse that had performed long-term exercise, for an hour a day, over a month in total.

As a result, as can be seen from FIG. 8, both short-term and long-term exercise groups exhibited an increase in the concentration of ATIF1 compared to the control group. This result suggests that ATIF1 is secreted from muscle tissue during exercise and is present at a high level in the blood, which means that myokine ATIF1 can also play a significant physiological role under actual in-vivo conditions and can be used clinically in the future.

Example 9: Effect of ATPIF1 on Improvement of Glucose Tolerance in Animal Experiments Type 2 diabetes model dbdb mice (Central Lab Animal Inc., CLA) were subjected to GTT (glucose tolerance test) to identify whether or not insulin resistance was improved after intraperitoneal administration of recombinant protein, ATPIF1 protein at a concentration of 5 mg/kg for 10 weeks.

Figure 9:
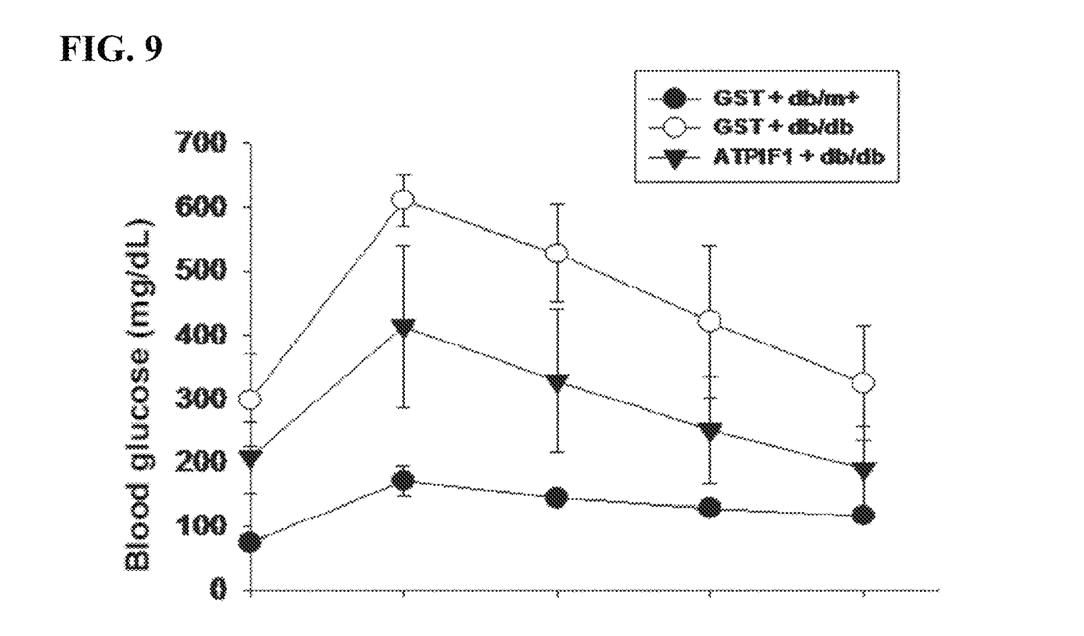
FIG. 9 shows the results of a GTT (glucose tolerance test) conducted after intraperitoneal administration of recombinant ATPIF1 proteins to type 2 diabetes model dbdb mice for a month.

As a result, as can be seen from FIG. 9, the mice administered with ATPIF1 exhibited an increase in blood glucose levels compared to the control group or mice administered only with GST. This result means that ATPIF1 can perform glycolic control by improving insulin resistance.

INDUSTRIAL APPLICABILITY

The composition containing ATPIF1 according to the present invention has a therapeutic effect on diabetes by promoting glucose uptake in muscle cells and improving insulin sensitivity, and also has an effect of inhibiting fat synthesis in adipocytes and promoting browning of adipocytes, thereby being effective in preventing or treating obesity.

Although specific configurations of the present invention have been described in detail, those skilled in the art will appreciate that this detailed description is provided as preferred embodiments and should not be construed as limiting the scope of the present invention. Therefore, the substantial scope of the present invention is defined by the accompanying filed claims and equivalents thereto.

SEQUENCE LISTING FREE TEXT

An electronic file is attached.

The invention claimed is:

1. A method for preventing or treating a diabetic condition in which diabetic retinopathy is not present, comprising administering a peptide consisting of the sequence of SEQ ID NO: 1, further comprising administering insulin or an insulin analog.

2. The method according to claim 1, wherein the diabetic condition is type 1 diabetes or type 2 diabetes.

3. The method according to claim 1, wherein the diabetic condition comprises at least one selected from diabetic nephropathy, hyperlipidemia, and fatty liver.

4. The method according to claim 1, wherein the peptide promotes insulin sensitivity.

* * * * *

UNITED STATES PATENT AND TRADEMARK OFFICE
CERTIFICATE OF CORRECTION

PATENT NO. : 10,946,060 B2
APPLICATION NO. : 16/494293
DATED : March 16, 2021
INVENTOR(S) : Hyeon Soo Kim Page 1 of 1

It is certified that error appears in the above-identified patent and that said Letters Patent is hereby corrected as shown below:

On the Title Page

Page 2, in Line 2 of the reference listing for Nakamura et al. under "OTHER PUBLICATIONS", "growth breeding" should be -- growth and breeding --.

In the Specification

Column 3, Line 45, "ATPIF1in" should be -- ATPIF1 in --.

Column 5, Line 1, "type diabetes" should be -- type 1 diabetes --.

Signed and Sealed this
Twenty-fourth Day of September, 2024

Katherine Kelly Vidal
*Director of the United States Patent and Trademark Office*